(12) United States Patent
Yom-Tov

(10) Patent No.: US 8,022,229 B2
(45) Date of Patent: Sep. 20, 2011

(54) PROCESS FOR THE PREPARATION OF ALKYL 5-(DICARBOXIMIDO) LEVULINATE AND ALKYL 4-OXO-PENTENOATE

(75) Inventor: Baruch Yom-Tov, Lund (SE)

(73) Assignee: Alfa-Synthon AB, Lund (SE)

( * ) Notice: Subject to any disclaimer, the term of this patent is extended or adjusted under 35 U.S.C. 154(b) by 345 days.

(21) Appl. No.: 11/666,931

(22) PCT Filed: Nov. 2, 2005

(86) PCT No.: PCT/EP2005/011688
§ 371 (c)(1),
(2), (4) Date: Oct. 3, 2007

(87) PCT Pub. No.: WO2006/048236
PCT Pub. Date: May 11, 2006

(65) Prior Publication Data
US 2008/0027233 A1    Jan. 31, 2008

(30) Foreign Application Priority Data

Nov. 3, 2004 (SE) ...................... 0402679

(51) Int. Cl.
C07D 209/48 (2006.01)
C07C 67/317 (2006.01)
C07C 69/738 (2006.01)

(52) U.S. Cl. ...................... 548/473; 560/205
(58) Field of Classification Search .................. 548/473; 560/205
See application file for complete search history.

(56) References Cited

OTHER PUBLICATIONS

Benedikt et al. "Synthesis of 5-Aminolevulinic Acid" Verlag der Zeitschrift fur Naturforschung, 1986, pp. 1593-1594.*
Kulinkovich et al. "A Convenient Method for the Preparation of Methyl trans-4-Oxo-2-alkenoates" Synthesis, 1986, pp. 378-379.*
Gibson et al. "The Gabriel Synthesis of Primary Amines" Angew. Chem. Inter. Ed. Eng., 1968, vol. 7, pp. 919-930.*
MacDonalad "Methyl 5-Bromolevulinate" Can. J. Chem, 1974, vol. 52, pp. 3257-3258.*
Benedikt et al. "Synthesis of 5-Aminolevulinic Acid." *Zeitschrift fuer naturforschung. Teil b, Anorganische Chemi, Ogranische Chemie, Verlag Der Zeitschrift fuer Naturforschung*, Tuebingen. vol. 41B. 1986. pp. 1593-1594.
MacDonald et al. "Methyl 5-Bromolevulinate." *Can. J. Chem.* vol. 52. 1974. pp. 3257-3258.
Database CA 'Online' Chemical Abstracts Service. Zav'Yalov et al. "Synthesis of 5-amino-4-oxopentanoic acid hydrochloride.", Accessed 2006.
Kulinkovich et al. "A Convenient Method for Preparation of Methyl trans-4-Oxo-2-alkenoates." *Synthesis* No. 5. 1986. pp. 378-379.
Porter et al. "Steroselective Intermolecular Radical Additions to Amide-Substituted Alkenes." *J. Am. Chem. Soc.* vol. 113. 1991. pp. 1791-1799.
Zimmer et al. "6-Siloxy-Substituted 5,6-Dihydro-4H-1,2oxazines as Key Building Blocks for Natural Products." *Liebigs Ann. Chem.* 1992. pp. 709-714.
Database CA 'Online' Chemical Abstracts Service. Gao Xuesong. "Preparation of 5-aminolevulinic acid and its derivatives.", Accessed 2006.

* cited by examiner

*Primary Examiner* — Joseph Kosack
(74) *Attorney, Agent, or Firm* — Pierce Atwood, LLP; Kevin M. Farrell; David J. Wilson

(57) ABSTRACT

A method of manufacturing esters of dicarboxyimidolevulinic acid and alkyl trans-4-oxo-2-pentenoate. This method includes two reaction steps, wherein the first step of said two reaction steps is a bromination of alkyl-levulinate, to obtain alkyl-(3 and 5)-bromolevulinate, and the second step of said two reaction steps is a synthesis of esters of dicarboxyimidolevulinic acid and alkyl trans-4-oxo-2-pentenoate, by reacting the alkyl-(3 and 5)-bromolevulinate obtained in said first step with dicarboxyimide anion.

23 Claims, 1 Drawing Sheet

BrCH₂COCH₂CH₂COO-Alk.

CH₃COCHBrCH₂COO-Alk.

+

CH₃COCH=CHCOO-Alk.

+  + KBr

PROCESS FOR THE PREPARATION OF ALKYL 5-(DICARBOXIMIDO) LEVULINATE AND ALKYL 4-OXO-PENTENOATE

TECHNICAL FIELD

The present invention refers to a manufacturing process of esters of dicarboxyimidolevulinic acid and alkyl trans-4-oxo-2-pentenoate (such as methyl trans-β-acetylacrylate).

BACKGROUND OF THE INVENTION

Derivates of δ-aminolevulinic acid (DALA) have recently been the subject of extensive and increased investigation and research, because of their biological effects. New effects have been discovered for derivates of δ-aminolevulinic acid (DALA), such as anti-cancer effect, pesticide effect, and insecticide effect. This results in that derivates of DALA may be used in technical areas, such as anti-cancer agent, pesticide agent, insecticide agent, and as a plant growth factor.

Trans-4-oxo-2-pentenoate is also a compound of great chemical value, and it is therefore of great interest to find easy, economical and time saving methods to manufacture it. Trans-4-oxo-2-pentenoate is a reactive enone, that for example may be used in conjugate addition of ketones and similar compounds, such as for example Robinson annelations.

Neuberger, A. et al., J. Chem. Soc., 1954, p. 1820 describes the use of esters of 5-phtalimidolevulinic acid as precursors of DALA, through elimination of phtalic acid, by hydrolysis.

Lopez, R. F. V., et al., Adv. Drug Delivery Reviews, 56, p. 77-94, 2004, discloses the use of esters of δ-phtalimidolevulinic acid as a substitute for DALA, due to the relative stability in comparison to DALA, for instance when used as a PDT (photodynamic therapy) sensitizer.

Dabrowski Zbigniew et al., "The synthesis and application of 5-aminolevulinic acid derivatives in photodynamic therapy and photodiagnosis", Acta poloniae pharmaceutica, vol. 60, p. 219 to 224, 2003, describes a method to use ALA-esters in photodynamic therapy and photodiagnosis, in which method 5-bromoleulinate is reacted with phtalimide to obtain 5-phtalimidolevulinate. This method presents a number of disadvantages. Firstly, this method is in need of a distillation of the crude reaction mixture, obtained from the bromination of levulinic acid. Secondly, this method only reacts 5-bromo-leulinate with phtalimide, which presents the disadvantage of a need to purify the product in a cumbersome purifying step at a very low temperature, which step is costly and time spending. This purifying step also results in a reaction rest containing brominated contaminations (the brominated contaminations constitute 65% of the used crude material, according to the article). Thirdly, as a result of the reaction steps according to this article, no trans-4-oxo-2-pentenoate is obtained, which compound has a significant economic and scientific value.

Katsumi et al., "Synthesis of 5-[4,5-$^{13}$C2] and 5-[1,5-$^{13}$C2] aminolevulinic acid", Journal of labelled compounds and radiopharmaceuticals, pages 569 to 576, 2002, describes the reaction between phtalimide and ethyl bromo[1,2-$^{13}$C]acetate. The object in this article is not the same as the present invention, i.e. to obtain phtalimidolevulinic, or succinimidol-evulinic, acid and trans-4-oxo-2-pentenoate. Thereby, the steps performed in this article fails to disclose the combined obtainment of said substances. Furthermore, in this respect this article includes a six step manufacturing process of $C^{13}$ marked ALA, which manufacturing process is totally different from the present invention and has therefore used totally different substances. An intermediate product of this manufacturing process is however similar to one of the final products according to the present invention.

Other documents disclosing the state of the art are U.S. Pat. No. 5,907,058, which describes the manufacturing of aminolevulinic acid, and CN 1056868 and PL 104118, which two documents describes other reactions with phtalimide.

Hence, an improved method of manufacturing esters of dicarboxyimidolevulinic acid and alkyl trans-4-oxo-2-pentenoate (alkyl trans-β-acetylacrylate) would be advantageous and in particular needed to allow an increased yield, cost-effectiveness, time-effectiveness, and ease over the processes according to prior art, and it would be even more advantageous if esters of dicarboxyimidolevulinic acid and alkyl trans-4-oxo-2-pentenoate (alkyl trans-β-acetylacrylate) could be manufactured in the same reaction, said reaction being easy to operate, more economical than the processes according to the prior art, and that is time saving in comparison with the processes according to prior art. Furthermore, it would be of great advantage to provide a method of manufacturing esters of dicarboxyimidolevulinic acid and alkyl trans-4-oxo-2-pentenoate (alkyl trans-β-acetylacrylate) where cumbersome and costly distillation and purifying processes and the obtainment of brominated contaminations, according to the prior art, could be omitted.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a method according to the appended patent claims.

The general solution according to the invention is to provide a method, including a two step process to manufacture esters of dicarboxyimidolevulinic acid and alkyl trans-4-oxo-2-pentenoate (such as methyl trans-(β-acetylacrylate), wherein the first step of said two step process is a bromination of alkyl-levulinate, and the second step of said two step process is a synthesis of esters of dicarboxyimidolevulinic acid and alkyl trans-4-oxo-2-pentenoate from the mixture of alkyl-3-bromolevulinate and alkyl-5-bromolevulinate, obtained from said step of bromination of alkyl-levulinate.

According to one aspect of the invention, a method is provided that is time saving in comparison with the processes according to the prior art.

According to another aspect of the invention, a method is provided that is easy in comparison with the processes according to the prior art.

According to still another aspect of the invention, a method is provided that provides a higher yield than the processes according to the prior art.

According to still another aspect of the invention, a method, is provided that may be performed at lower temperature than the processes according to the prior art.

According to yet another aspect of the invention, a method is provided that is more economical than the processes according to the prior art.

According to yet another aspect of the invention, a method is provided, wherein both esters of δ-phtalimidolevulinic acid and alkyl trans-4-oxo-2-pentenoate are obtained.

According to still another aspect of the invention, a method is provided that does not include cumbersome and costly purification steps.

To fulfill these objects the present invention provides a method that is time saving, easy, and provides higher yield in comparison with the processes according to the prior art, and is more economical than the processes according to the prior art, and that provides both esters of dicarboxyimidolevulinic acid and alkyl trans-4-oxo-2-pentenoate, without unnecessary purification steps while still omitting the obtainment of brominated contaminations.

Preferred embodiments emerge from the dependent claims of the present application.

BRIEF DESCRIPTION OF DRAWINGS

These and other aspects, features and advantages of which the invention is capable of will be apparent and elucidated from the following description of embodiments of the present invention, reference being made to the accompanying drawings, in which.

DETAILED DESCRIPTION OF PREFERRED EMBODIMENTS

Figure 1:
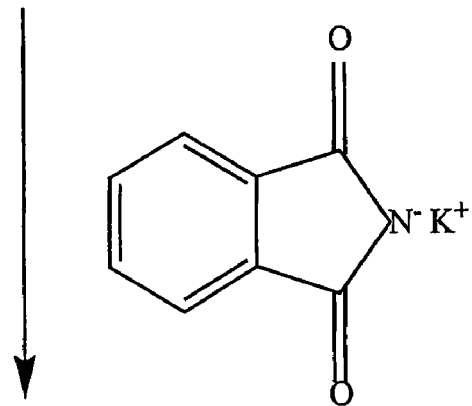
FIG. 1 is a reaction according to one embodiment of the present invention.
Figure 1:
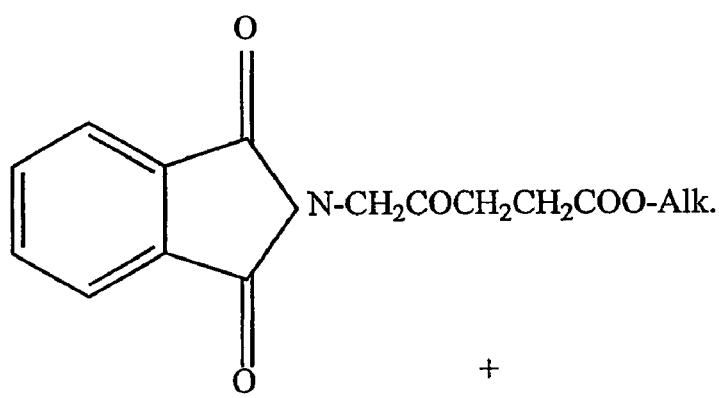
Figure 1:
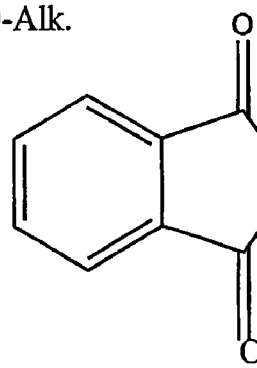

The following description focuses on an embodiment of the present invention applicable to a process of manufacturing. However, it will be appreciated that the invention is not limited to this application but may be applied to many other similar processes.

The process according to the present invention is performed in two steps: first a bromination of alkyl-levulinate, and thereafter, the synthesis of esters of dicarboxyimidolevulinic acid and alkyl trans-4-oxo-2-pentenoate.

When performing the step of bromination of methyl-levulinate, the procedure according to Hyun-Joon Ha et al. was modified, namely: the reaction time was reduced from 3.5 hours to 25 minutes, while the yield of the brominated ester was increased to approximately 96% (in Hyun-Joon Ha et al. the yield was 64%).

In one embodiment of the present invention, according to FIG. 1, 29.6 g levulinic acid (0.25 mole 98%), dissolved in 600 ml methanol (analytical 99.8%), was heated up to reflux. 40 g bromine (12.86 ml) was added dropwise, during stirring, to the refluxing levulinic acid solution in the following manner. The first three drops needed approximately 2 minutes initiation time to react (complete disappearance of the bromine). Then the addition was adjusted at the rate of disappearance of the bromine. The stirring continued for further two minutes, after the total amount of bromine had been added (approximately 25 minutes), until the solution was colourless.

The solvent was then distilled off by reduced pressure (or evaporation), until the volume of the reaction mixture reached 75 ml. A volume of approximately 80 ml ice cold water was added to the solution with stirring. Thereafter, a concentrated $NaHCO_3$ solution was carefully added until the solution reached neutral.

The product, which is an organic mixture that has a higher density than water, was extracted with 25 ml ethylacetate, and the lower layer (ethylacetate phase) was separated. The upper layer (water phase) was then extracted additionally two times with 40 ml ethylacetate. The combined organic layer (the three ethylacetate phases) was then drained (there was no need to dry the solution, since the moisture content is azotroped out together with the solvent during evaporation), and the solvent evaporated under reduced pressure. The obtained product was a mixture of alkyl-3-bromolevulinate and alkyl-5-bromolevulinate. Said mixture (50.5 g (96.6%) of a colorless oily substance) was dry enough to be used without further treatment in the step of synthesis, according to FIG. 1.

The step of syntheses of esters of dicarboxyimidolevulinic acid and alkyl trans-4-oxo-2-pentenoate, according to FIG. 1, was initiated by adding 20.9 g of the crude brominated product (a mixture of methyl-3-bromolevulinate and methyl-5-bromolevulinate, obtained from said step of bromination of methyl-levulinate) dropwise to a suspension of 20 g K-phtalimide in dry N,N-dimethylformamide (DMF), which was cooled on an ice bath, with stirring. The phtalimide used above may naturally be any kind of phtalimide, preferably an alkali metal phtalimide, such as K-phtalimide, Na-phtalimide, etc., or tertiary amine phtalimide, such as triethylamine phtalimide, pyridine phtalimide, etc. The rate of addition was adjusted in such a way that the reaction temperature did not exceed 5° C. (this reaction is exotermic). After all of the crude brominated product, obtained above, was added (approximately 15 minutes) an additional amount of 5 ml DMF was washed in. The obtained pale pink suspension was stirred, during cooling in an ice bath, for an additional 15 to 20 minutes. Thereafter, 45 ml of a cold (such as between 0 to 10° C., such as 0 to 5° C.) 2N HCl solution was added under vigorous stirring during 1 to 2 minutes.

This was followed by an addition of 250 ml cold water (approximately 0 to 15° C., such as 0 to 5° C.) in a separation step. A white precipitation was obtained, which was refrigerated over night. Thereafter, the precipitation was filtered off and washed two times with cold water (approximately 0 to 15° C., such as 0 to 5° C.). The combined water solution (the filtrate) was kept for later treatment. The filtered product was triturated with 120 ml toluene and then filtered off again. This procedure was repeated two times with 40 ml toluene each time.

The insoluble white material which remained (phtalimide) was filtered off, and evaporation of the toluene solution, by reduced pressure, gave approximately 15 g crystals of methyl δ-phtalimidolevulinate (melting point approximately 92 to 93° C.). Recrystallisation from 20 ml toluene gave 13.8 g (50.2%) of an almost pure white crystalline product (melting point 96 to 97° C.) (96 to 97° C., according to Neuberger et al.).

The filtrate obtained above was extracted with ethylacetate. Evaporation of the ethylacetate gave an oil (6.2 g), which solidified at room temperature (melting point 60.5 to 61° C. (ether/PE)). The obtained compound was methyl trans-4-oxo-2-pentenoate (methyl trans-β-acetylacrylate).

In this embodiment DMF was used as a solvent. Naturally, any solvent that is soluble in water can be used, such as methanol, ethanol, DMSO, tetrahydrofuran, etc.

In other embodiments of the present invention the methyl group on the methyl-levulinate was replaced by any other suitable alkyl, such as ethyl, propyl, butyl, pentyl, hexyl, heptyl, octyl, nonyl, decyl etc., but this invention is not limited to these examples.

In still other embodiments of the present invention other dicarboxylmides than phtalimide is used. Such dicarboxylmides may for example be chosen from the group comprising succinimide, 1,8 naphtalimide, maleimide, hydantoin, diphenicimide, etc., but this invention is not limited to these examples. In these embodiments of the present invention the obtained dicarboxyimidolevulinate may be 1,8 naphtalimidolevulinate, maleimdolevulinate, hydantionlevulinate, or diphenicimidolevulinate.

While the invention has been described in connection with specific embodiments thereof, it will be understood that it is capable of further modifications, and this application is intended to cover any variations, uses, or adaptations of the invention following, in general, the principles of the invention and including such departures from the present disclosure as come within known or customary practice in the art to which the invention pertains and as may applied to the essential features hereinabove set forth, and as fall within the scope of the invention and the limits of the appended claims.

Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc do not preclude a plurality.

The invention claimed is:

1. A method of manufacturing esters of dicarboxyimidolevulinic acid and alkyl trans-4-oxo-2-pentenoate, comprising a first step of bromination of alkylic levulinate, to obtain a mixture of alkyl-3-bromolevulinate and alkyl-5-bromolevulinate, and a second step of synthesis of esters of dicarboxyimidolevulinic acid and alkyl trans-4-oxo-2-pentenoate, by reacting the alkyl-3-bromolevulinate/alkyl-5-bromolevulinate mixture, obtained in said first step, with a dicarboxylmide anion, and a third step of separation of esters of dicarboxyimidolevulinic acid and alkyl trans-4-oxo-2-pentenoate.

2. Method according to claim 1, wherein said dicarboxylmide is phtalimide, 1,8 naphtalimide, maleimide, hydantoin, diphenicimide, or succinimide, whereby said synthesized esters of dicarboxyimidolevulinic acid is esters of δ-phtalimidolevulinic acid, esters of 1,8 naphtalimidolevulinic acid, esters of maleimidolevulinic acid, esters of hydantionlevulinic acid, esters of diphenicimidolevulinic acid, or esters of succinimidolevulinic acid.

3. Method according to claim 1, wherein said alkyl is methyl or ethyl.

4. Method according to claim 1, wherein said separation is performed by precipitation in a water solution.

5. Method according to claim 4, wherein said esters of dicarboxyimidolevulinic acid are obtained in a precipitation after said precipitation in water.

6. Method according to claim 4, wherein said alkyl trans-4-oxo-2-pentenoate is obtained in said water solution.

7. Method according to claim 6, wherein said alkyl trans-4-oxo-2-pentenoate is extracted from said water solution.

8. Method according to claim 7, wherein said extraction is performed with ethylacetate.

9. Method according to claim 8, followed by evaporation of said ethylacetate.

10. Method according to claim 4, wherein esters of dicarboxyimidolevulinic acid are purified by trituration with toluene, followed by evaporation of said toluene.

11. A method of manufacturing esters of dicarboxyimidolevulinic acid and alkyl trans-4-oxo-2-pentenoate, comprising a first step of bromination of alkylic levulinate, achieved by adding bromine to a refluxing levulinic acid solution at the approximate rate of disappearance of the bromine and wherein the bromination reaction time is approximately 25 minutes to obtain a mixture of alkyl-3-bromolevulinate and alkyl-5-bromolevulinate, and a second step of synthesis of esters of dicarboxyimidolevulinic acid and alkyl trans-4-oxo-2-pentenoate, by reacting the alkyl-3-bromolevulinate/alkyl-5-bromolevulinate mixture, obtained in said first step, with a dicarboxylmide anion.

12. Method according to claim 11, wherein said dicarboxylmide is phtalimide, 1,8 naphtalimide, maleimide, hydantoin, diphenicimide, or succinimide, whereby said synthesized esters of dicarboxyimidolevulinic acid is esters of δ-phtalimidolevulinic acid, esters of 1,8 naphtalimidolevulinic acid, esters of maleimidolevulinic acid, esters of hydantionlevulinic acid, esters of diphenicimidolevulinic acid, or esters of succinimidolevulinic acid.

13. Method according to claim 11, wherein said alkyl is methyl or ethyl.

14. Method according to claim 11, comprising a third step of separation of esters of dicarboxyimidolevulinic acid and alkyl trans-4-oxo-2-pentenoate.

15. Method according to claim 14, wherein said esters of dicarboxyimidolevulinic acid are obtained in a precipitation in water.

16. Method according to claim 14, wherein alkyl trans-4-oxo-2-pentenoate is obtained in said water solution.

17. Method according to claim 16, wherein said alkyl trans-4-oxo-2-pentenoate is extracted from said water solution.

18. Method according to claim 17, wherein said extraction is performed with ethylacetate.

19. Method according to claim 18, followed by evaporation of said ethylacetate.

20. Method according to claim 14, wherein esters of dicarboxyimidolevulinic acid are purified by trituration with toluene, followed by evaporation of said toluene.

21. The method of claim 11, wherein said bromine is added step-wise to the refluxing levulinic acid solution.

22. The method of claim 11, wherein said bromine is added continuously to the refluxing levulinic acid solution.

23. The method of claim 11, wherein the yield of alkyl-3-bromolevulinate and alkyl-5-bromolevulinate is greater than 90%.

* * * * *